(12) United States Patent
Dulguerov

(10) Patent No.: US 6,706,017 B1
(45) Date of Patent: Mar. 16, 2004

(54) PERCUTANEOUS OSTOMY DEVICE AND METHOD FOR CREATING A STOMA AND IMPLANTING A CANULA

(76) Inventor: Pavel Dulguerov, 34 route de Givrins, CH-1276 Gingins (CH)

(*) Notice: Subject to any disclaimer, the term of this patent is extended or adjusted under 35 U.S.C. 154(b) by 0 days.

(21) Appl. No.: 09/663,773

(22) Filed: Sep. 18, 2000

(51) Int. Cl.[7] .................. A61M 5/178; A61M 16/00
(52) U.S. Cl. ..................... 604/164.01; 128/207.29
(58) Field of Search .................. 604/95.03, 96.01, 604/161, 164.01, 170.03, 164.03, 264, 164.1, 910; 606/191, 192, 194, 108; 128/207.29, 207.26, 207.14

(56) References Cited

U.S. PATENT DOCUMENTS

| | | |
|---|---|---|
| 2,548,602 A | 4/1951 | Greenburg |
| 2,991,787 A | 7/1961 | Shelden et al. |
| 3,511,243 A | 5/1970 | Toy |
| 3,833,003 A | 9/1974 | Taricco |
| 3,848,605 A | 11/1974 | Harautuneian et al. |
| 4,471,778 A | 9/1984 | Toye |
| 4,589,868 A | 5/1986 | Dretler |
| 4,622,968 A | 11/1986 | Persson |
| 4,817,598 A * | 4/1989 | LaBombard ............ 128/207.14 |
| 4,889,112 A | 12/1989 | Schachner et al. |
| 5,058,580 A | 10/1991 | Hazard |
| 5,160,321 A * | 11/1992 | Sahota ................ 604/101.03 |
| 5,176,659 A * | 1/1993 | Mancini ................... 604/523 |
| 5,183,464 A | 2/1993 | Dubrul et al. |
| 5,217,005 A | 6/1993 | Weinstein |
| 5,279,285 A | 1/1994 | Griggs |
| 5,297,546 A | 3/1994 | Spofford et al. |
| 5,431,676 A | 7/1995 | Dubrul et al. |
| 5,569,184 A | 10/1996 | Crocker et al. |
| 5,573,517 A | 11/1996 | Bonutti et al. |
| 5,653,230 A | 8/1997 | Ciaglia et al. |
| 5,690,669 A | 11/1997 | Sauer et al. |
| 5,817,062 A | 10/1998 | Flom et al. |
| 5,840,013 A * | 11/1998 | Lee et al. .................. 600/114 |
| 5,964,223 A * | 10/1999 | Baran ................... 128/200.14 |
| 6,283,951 B1 * | 9/2001 | Flaherty et al. ......... 604/164.11 |
| 6,371,943 B1 * | 4/2002 | Racz et al. ................. 604/264 |

OTHER PUBLICATIONS

Toy, et al., "A Percutaneous Tracheostomy Device", *Surgery*, vol. 65, No. 2, pp. 384–389 (1969).

(List continued on next page.)

*Primary Examiner*—Manuel Mendez
*Assistant Examiner*—Mark K Han
(74) *Attorney, Agent, or Firm*—Hoffman & Baron, LLP

(57) ABSTRACT

An ostomy device and method for creating a stoma and implanting a canula. The ostomy device includes an elongate needle having a sharpened tip for percutaneous entry of a body forming a stoma. The needle includes a plurality of channels extending axially through the needle, and each of the plurality of channels having a distal end adjacent the needle tip. The channels permit the monitoring of the needle tip to assist in properly locating the needle within the body. A dilation device is disposed about the distal end of the needle and is insertable within the stoma. The dilation device including a radially expandable surface to dilate the stoma for atraumatic receipt of a canula. The dilation device may include a primary dilator for dilating the stoma a first degree and a secondary dilator for dilating the stoma a second degree such that canula may be atraumatically implanted.

31 Claims, 9 Drawing Sheets

OTHER PUBLICATIONS

Toye, et al., "Clinical Experience with Percutaneous Tracheostomy and Cricothyroidotomy in 100 Patients", *The Journal of Trauma*, vol. 26., No. 11, pp. 1034–1040 (1986).

Ciaglia, et al., "Elective Percutaneous Dilatational Tracheostomy—A New Simple Bedside Procedure; Preliminary Report", *Chest*, vol. 87, No. 6, pp. 715–719 (1985).

Schachner, et al., "Percutaneous Tracheostomy—A New Method", *Critical Care Medicine*, vol. 17, No. 10, pp. 1052–1056 (1989).

Wang, et al., "Early Experience with Percutaneous Tracheotomy", *Laryngoscope* 102, pp. 157–162 (1992).

Caldicott, et al., "An Evaluation of a New Percutaneous Tracheostomy Kit", *Anaesthesia*, vol. 50, pp. 49–51 (1995).

Wilson, et al., "Percutaneous Tracheostomy", *British Journal of Hospital Medicine*, vol. 49, No. 2, pp. 123–126 (1993).

Dulguerov, et al., "Percutaneous or surgical tracheostomy: A meta–analysis", *Crit. Care Med.*, vol. 27, pp.1617–1625, (1999).

"R.E.D. Radially Expanding Dilator", Product Literature, InnerDyne Medical, Inc. (undated).

"Ciaglia Suggested Instructions for Percutaneous Tracheostomy Introducer Set", Cook Critical Care, Product Instructions, (Undated).

"Ciaglia Percutaneous Tracheostomy Introducer Set", Product Literature, Cook Critical Care, (1987).

"Percutaneous Dilatational Tracheostomy", Product Literature, Cook Critical Care (1994).

"SIMS Per–Fit Percutaneous Tracheostomy Kits", Product Literature, Smiths Industries Medical Systems (1995).

* cited by examiner

PERCUTANEOUS OSTOMY DEVICE AND METHOD FOR CREATING A STOMA AND IMPLANTING A CANULA

BACKGROUND OF THE INVENTION

The present invention related to a device for performing a percutaneous ostomy in a body, in particular a tracheostomy. More specifically, the present invention relates to a device and method for atraumatically forming and dilating a tracheostoma and implanting a tracheostomy canula therein.

Tracheostomy is the surgical creation of an opening, tracheostoma, between the trachea and the anterior neck skin, through which opening a tracheostomy canula is placed. This canula directs outside air to the lungs and permits breathing to bypass the upper aerodigestive tract (nose, mouth, pharynx and larynx). Tracheostomy can be performed emergently or electively. In elective tracheostomy patients are usually intubated by means of an endotracheal tube placed through the nose or mouth within the trachea.

Surgical tracheostomy was first codified in the early 1900s by Chevalier Jackson and has become a fairly common and standard procedure. The procedure involves incising the skin, dissecting the pre-tracheal musculature and directly exposing the anterior tracheal wall, which is opened, allowing for the placement of the canula. The tracheostomy canula is a hollow tube typically including a circumferential inflatable cuff. The hollow tube allows for the passage of air necessary for breathing or artificial ventilation and the inflatable cuff provides for a seal between the upper aerodigestive tract and the lower trachea and bronchi, protecting the lungs from fluids and foreign matter. The tracheostomy canula is left in place for a duration, varying from a few days to several years.

Like any procedure, surgical tracheostomy is associated with various risks and complications. In view of the relatively high frequency of tracheostomy complications, a new procedure was developed known as percutaneous tracheostomy. In percutaneous tracheostomy, a puncture is made with a needle through the skin and the needle tip is placed in the trachea. With most currently available devices, some form of a guide wire is then placed through the needle into the trachea and used for the introduction of one or several dilators in order to achieve an opening large enough to allow the introduction of the tracheostomy canula. A variation on this dilatation method is the use of metal spreaders inserted over the needle or the guide wire and used by mechanical spreading to enlarge the opening.

Several devices which are used for performing a percutaneous tracheostomy have been described in the medical literature and/or have been commercialized: In 1969, Toy and Weinstein [Toy F J, Weinstein J D: A percutaneous tracheostomy device. Surgery 65:384–389,1969] described a device using a needle through which a polyethylene tubing is introduced. After removal of the needle, "a bougie, onto which is fixed an endotracheal tube size 5, is then introduced onto the tubing; and the entire device is then thrust by means of a handle fixed on the bougie down into the trachea". This device was later modified [Toy F J, Weinstein J D: Clinical experience with percutaneous tracheostomy and cricothyroidotomy in 100 patients. J Trauma 26:1034–1040,1986] by incorporating the polyethylene guide onto the bougie-handle piece. This required the use of a needle that is either split or has a slot allowing its removal while the plastic guide remains in place.

Another percutaneous tracheotomy device was proposed by Ciglia et al. [Ciglia P, Firsching R, Syniec C: Elective percutaneous dilatational tracheostomy. A new simple bedside procedure; preliminary report. *Chest* 87:715–719, 1985]. This technique also uses a needle to puncture the trachea; a guide wire is placed through the needle and 8 dilators of progressively larger diameter are passed over the guide wire to dilate the opening. The canula is than threaded over a mid-size dilator and pushed over the guide wire into the tracheal lumen. A similar device and other devices incorporating minor modifications are commercially available.

A further tracheostomy device is named Rapitrac and was first described by Schachner et al. in 1989 [Schachner A, Ovil Y, Sidi J, Rogev M, Heilbron Y, Levy M J: Percutaneous tracheostomy—a new method. *Crit Care Med* 17:1052–1056,1989]. In this device the dilatation is achieved by a metal conus, incorporating a split in the center. The conus is inserted blindly over the needle used for the initial tracheal puncture. This conus is attached to a pair of plastic handles that are squeezed to achieve the dilatation.

Dilators for expanding body tissue having inflatable members are also known in the art. One such device is disclosed in U.S. Pat. No. 5,690,669 to Sauer et al. Sauer discloses a dilator having a fluid dispenser connected to an inflatable member that is insertable through a previously formed incision. The dilator is led to the proper location by way of a guide wire which has been inserted into the body. Once in the proper location, the fluid dispenser is activated to expand the inflatable member and adjacent body tissue. The use of this device however requires an initial incision and the use of a guide wire to properly locate the inflatable member. Furthermore, absent the use of imaging equipment, there is no way to ensure that the inflatable member is properly placed.

A further inflatable dilator is disclosed in U.S. Pat. No. 5,653,230 to Ciaglia et al. A balloon dilational tracheostomy device is disclosed which is used in conjunction with a guide wire to perform a tracheostomy. The device includes a balloon catheter extending through a hollow dilation tube. A tracheal tube or canula is insertable over the dilation tube. In order to use the device, a needle is percutaneously inserted into the trachea and a guide wire is inserted through the needle across the tracheal wall. The needle is then removed and the catheter is threaded over the guide wire and advanced into the trachea. Once in position, the balloon is inflated to create the dilated stoma. The tracheal canula and catheter are advanced until the canula is properly positioned. The catheter may then be removed leaving the canula in place. As with the Sauer device, Ciaglia requires an initial incision and the use of a guide wire. There is also no specific way to determine the precise location of the dilation device within the body.

The above described devices, however, all present difficulties in performing a pecutaneous tracheostomy. Use of the above devices includes uncertainty about the exact location of the needle tip and difficulty confirming that the needle tip is within the tracheal lumen. In order to circumvent these difficulties, it has been suggested that the endotracheal placement of the needle tip can be confirmed by the use of bronchoscopy. The bronchoscope is passed through the endotracheal tube, but this in itself can lead to other problems such as difficulty ventilating the patient and inadvertent extubation. Bronchoscopy is also expensive due to the specialized light sources and equipment required.

Use of a guide wire also leads to complications such as tissue lesions and loss of the tracheostomy pathway because of inadvertent kinking and displacement of the guide wire.

Furthermore, the use of numerous dilators in order to achieve the necessary opening for placing the tracheostomy canula is problematic. Such a system is time consuming and includes the possibility of creating tissue lesions and a false passage. Furthermore, once the largest of the series of dilators is placed, the introduction of the tracheal canula is often difficult because there is no protection for the tracheostomy cuff during its introduction and this sometimes results in a rupture of the cuff. The dilators are also not adapted for all the available tracheostomy canula.

Moreover, positioning of the dilators may also lead to complication. Over insertion of a pointed dilator may inadvertently cause a lesion of the posterior tracheal wall, which could result in serious infections and even death.

Accordingly, it would be desirable to provide a device for expanding body tissue which both creates a stoma in a body and atraumatically dilates the stoma without the need for a guide wire. It would also be desirable to provide a device for expanding body tissue providing the ability to determining the location of the device in the body to ensure proper placement thereof. It would further be desirable to provide a method of expanding body tissue which does not require a guide wire or separate procedure to form the initial opening in the body.

SUMMARY OF THE INVENTION

It is an advantage of the present invention to provide an ostomy device for creating an anatomical stoma.

It is another advantage of the present invention to provide an ostomy device for creating and atraumatically dilating an anatomical stoma and implanting a canula into the stoma.

It is a further advantage of the present invention to provide an ostomy device having a needle including a plurality of channels extending longitudinally there through in order to permit. The needle having a dilation device secured thereto for creating and dilating a stoma, thereby permitting the implantation of a canula in the stoma.

It is still a further advantage of the present invention to provide an ostomy device for creating and dilating a stoma and implanting a canula, the ostomy device including a needle for forming an initial stoma and an inflatable dilation device secured to a distal portion of the needle. A canula is insertable over the needle and advancable thereon. Upon insertion across the pretrachael tissues and tracheal wall, the dilation device dilates the stoma permitting the canula to be advanced along the needle into the tracheal lumen.

It is yet a further advantage of the present invention to provide a method of implanting a tracheal canula.

In the efficient attainment of these and other advantages, the present invention provides an ostomy device having an elongate needle having a sharpened tip for percutaneous entry of a body forming a stoma. The needle including a plurality of channels extending axially through the needle and each of the plurality of channels having a distal end adjacent the needle tip. A dilation device is disposed about the distal end of the needle and insertable within the stoma. The dilation device includes a radially expandable surface to dilate the stoma for atraumatic receipt of a tracheostomy canula.

The present invention also provides a tracheostomy device including a needle having an opening extending axially there through and having a sharpened tip for forming a tracheostoma in a tracheal wall. The distal end of the needle has a gradually curved portion for preventing injury to the posterior tracheal wall. An inflatable dilation device being in fluid communication with a fluid source and being secured about the needle and insertable within the tracheostoma. The dilation device including a surface being radially expandable upon introduction of a fluid in the dilation device to dilate the tracheostonia for receiving a tracheostomy canula. A radially expandable sheath is disposed about the dilation device and is radially expandable upon expansion of the dilation device.

The present invention further provides a tracheostomy device including a needle having a passage extending axially there through and having a distal portion ending in a tip for forming a stoma in a tracheal wall. A dilation device is adapted to be inserted in the tracheostoma and is provided and includes a first dilator disposed about the needle and being diametrically expandable to provide a first degree of stoma dilation. The dilation device further includes a second dilator disposed about the first dilator and adjacent the distal end of the needle and being insertable within the stoma. The second dilator includes a diametrically expandable surface to provide a second degree of stoma dilation whereby the stoma is capable of atraumatically receiving a tracheostomy canula.

The present invention still further provides a method of implanting a tracheal canula including the steps of:
 providing a tracheostomy device including a needle having a sharpened tip and having a diametrically expandable dilator disposed about a distal end of the needle;
 positioning a tracheal canula over the tracheostomy device;
 inserting the needle through the tracheal wall without the use of a guide wire to form a tracheostoma;
 monitoring the conditions at the needle tip during insertion of the needle in order to determine the anatomical location of the needle tip;
 expanding the dilator to atraumatically dilate the tracheostoma;
 contracting the dilator;
 advancing the canula over the needle into the dilated tracheostoma; and
 removing the tracheostomy device from the tracheostoma.

A preferred form of the ostomy device, as well as other embodiments, objects, features and advantages of this invention, will be apparent from the following detailed description of illustrative embodiments thereof, which is to be read in connection with the accompanying drawings.

DETAILED DESCRIPTION OF THE PREFERRED EMBODIMENTS

The present invention provides an ostomy device and method capable of creating a stoma and atraumatically dilating the stoma and inserting a canula through the dilated stoma to provide an unobstructed passageway into a body. The ostomy device is particularly suited for use in a tracheostomy wherein an opening in the pretracheal tissues and tracheal wall is created and a tracheostomy canula or tube is inserted therein. This description will describe the present invention in the context of the percutaneous tracheostomy procedure, but it is to be understood that the present invention may be employed in a wide range of medical ostomy procedures such as percutaneous access to various hollow organs such as abdominal cavity, uterus, thorax, articulation cavities etc., as well as non-hollow organs where cavity creation and other manipulations can take place.

Figure 1:
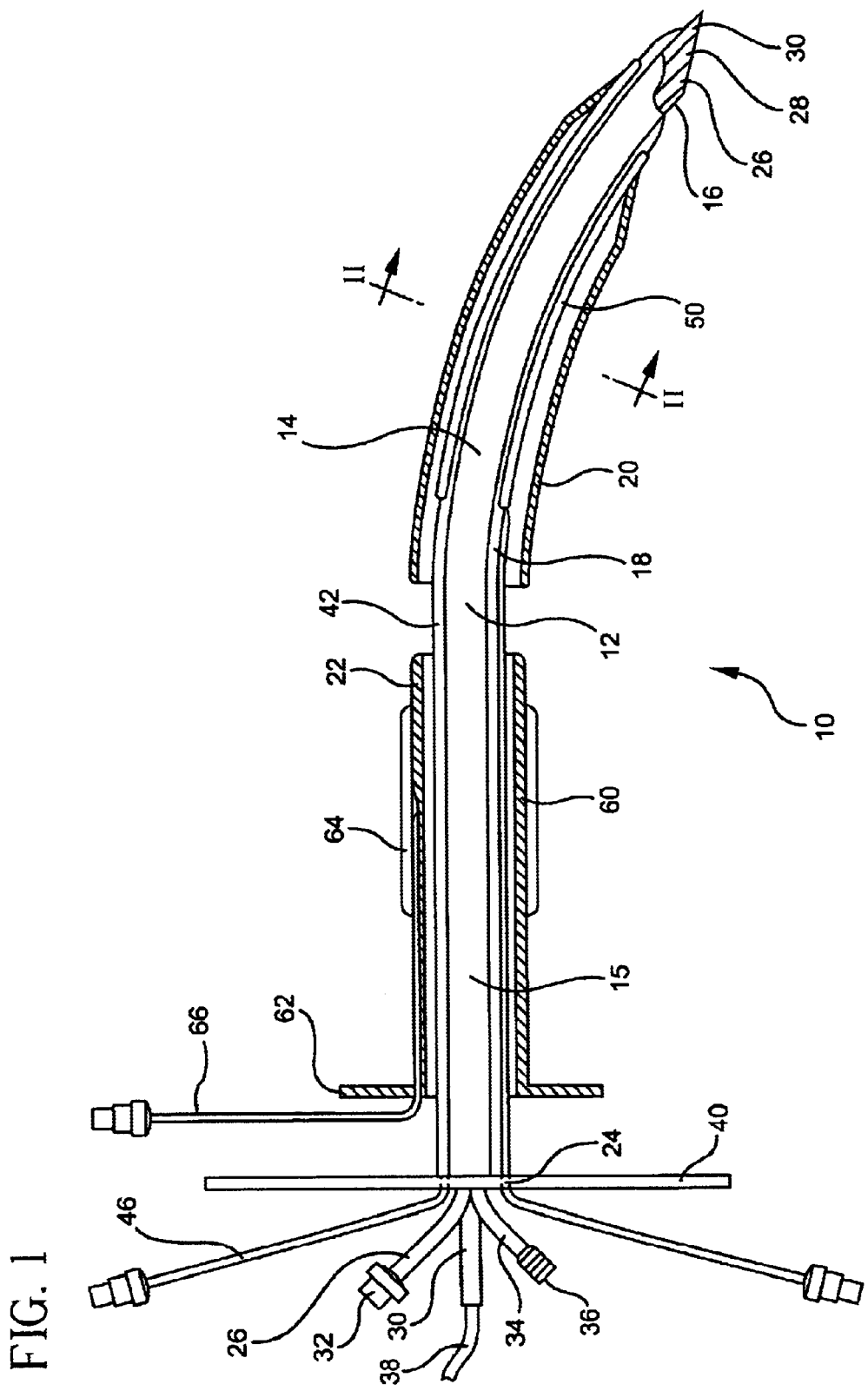
FIG. 1 is a side longitudinal cross-sectional view of the ostomy device of the present invention.
Figure 2:
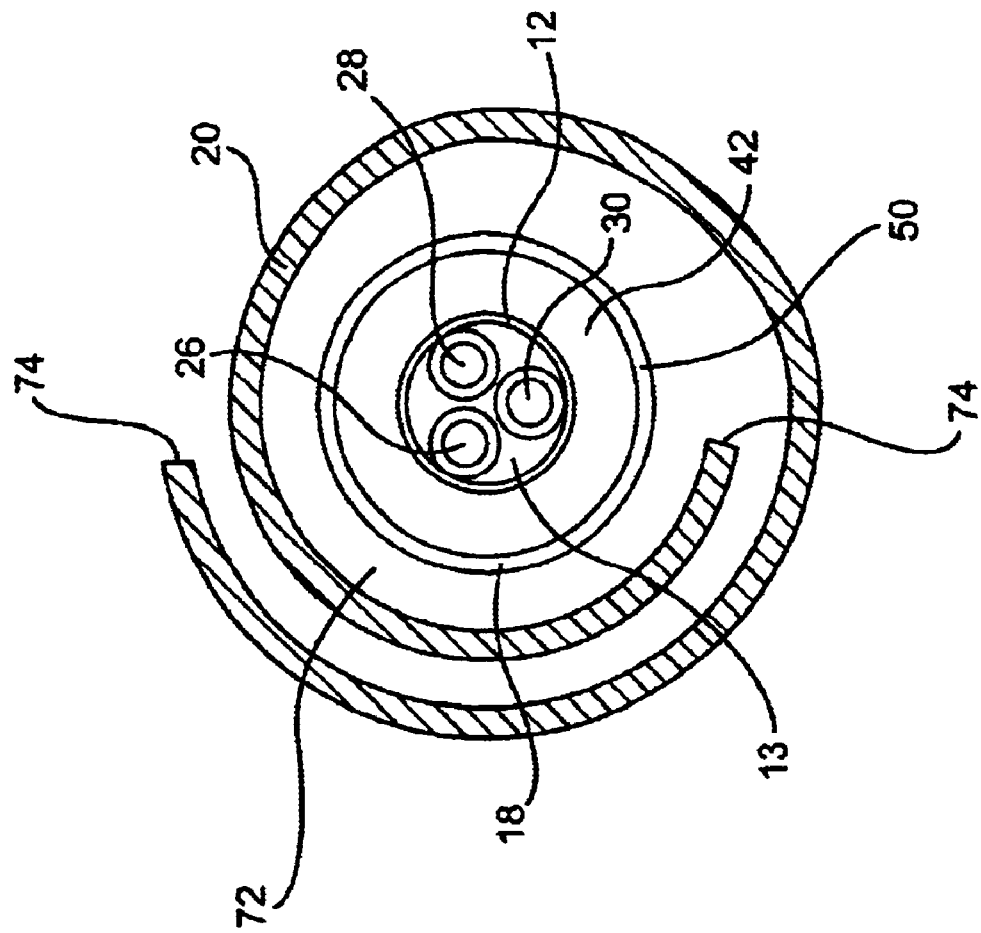
FIG. 2 is a cross-sectional view taken along line II—II of FIG. 1.

With reference to FIGS. 1 and 2, ostomy device 10 of the present invention generally includes an elongate needle 12 having a distal portion 14 ending in a sharpened tip 16. A selectively radially expandable dilation device 18 surrounds needle 12. A sheath 20 is disposed about dilation device 18 adjacent needle distal end 14. A canula 22 of a type well known in the art may be slidingly positioned over needle 12 and advancable from a needle proximal end 24 toward needle distal end 14. Ostomy device 10 is capable of creating and atraumatically dilating a stoma and implanting a canula to maintain a passageway into a body.

Needle 12 of the present invention is an elongate member having a passage 13 extending there through. Needle 12 may be formed of surgical steel, synthetic plastic, or other comparable material known in the surgical arts. Needle 12 includes a relatively straight proximal portion 15 that leads to a gradually curved distal portion 14 that is postionable within the body. The curved shape aids in preventing lesions of the posterior tracheal wall and the insertion of canula 22 during a tracheostomy procedure. The shape of needle 12 could be differently configured to accommodate ostomy procedures performed on other anatomical regions. Needle 12 may further include a handle 40 at a needle proximal end in order to assist an operator in manipulating needle 12 during a procedure. The needle is insertable through the skin and advancable into the tracheal lumen forming a relatively narrow tracheostoma.

In the performance of an ostomy procedure, and in particular a percutaneous tracheostomy, it is important to know the anatomical location of the needle tip in order to determine when the tracheal lumen has been entered and to avoid complications associated with needle misplacement. Accordingly, ostomy device 10 of the present invention provides for the proper anatomical positioning of needle 12. As shown in FIG. 2, needle passage 13 includes a plurality of lumen or channels 26, 28 and 30 extending along the length thereof. The channels may be formed by lengths of flexible tubing extending through needle 12, or alternatively, they be formed integrally with needle 12. The distal end of channels 26, 28 and 30 is substantially aligned with needle tip 16.

Each of channels 26, 28 and 30 each provide for an alternative way to determine the conditions at needle tip 16 during the procedure. This information is then used by an operator of ostomy device 10 to determine with a degree of specificity the anatomical location of the needle tip. One of the channels, channel 26, preferably provides a passage to withdraw air as needle 12 is advanced. The proximal end of channel 26 allows the attachment of a syringe to a proximal locking port 32 to withdraw air. The ability to aspirate air in front of needle can demonstrate air bubbles within a fluid-filled syringe connected to port 32, signaling the penetration within the tracheal lumen. In other applications, such as endoscopic surgery air could be injected through channel 26, allowing for tissue dissection and better visualization in front of the advancing needle tip.

Second channel 28 may be operatively connected to a $CO_2$ monitoring apparatus of the type that is routinely available in most operating or intensive care settings. The connection may be made by way of flexible tube 34 having a fitting 36 of a type well known in the art. The detection of $CO_2$ indicates that the needle tip 16 has entered the tracheal lumen. Furthermore, $CO_2$ monitoring can be used during slow needle advancement to signal that the tracheal wall has been punctured, a significant advance in adult and pediatric patients with thin tracheal walls.

A third channel, channel 30, may permit the introduction of a flexible fibroscope 38 that allows the visualization of the anatomic location of needle tip 16 throughout the procedure. Fibroscope 38 may be of a type commercially available having an outer diameter of about 1 mm. The fibroscope 38 may be attached to a camera and video display to enable the position of needle 12 to be monitored by the entire operating team. Fibroscope 38 may be used after placement of needle tip 16 within the trachea as indicated by the previously described $CO_2$ monitoring technique. Once needle 16 enters the trachea, an operator may view the progression of needle 12 within the trachea. Alternatively, fibroscope 38 may be placed within channel 30 from the beginning of the procedure to monitor the progression of needle 12 through the tissue planes of the neck and the tracheal wall puncture, thereby providing a direct visual control of the needle tip location through the entire procedure. While needle preferably includes three channels, it is within the contemplation of the present invention that two or four channels could be used for different purposes, as required by the particular ostomy performed. For tracheostomy, an optional use of channel could be to insufflate oxygen throughout the procedure into the trachea for respiration, as known in the art under the name of jet ventilation. For other ostomy procedures, suction of blood and debris can be a potential purpose.

The present invention permits monitoring through the different channels to be continued throughout the procedure assuring that an adequate intratracheal position is maintained. The ability to monitor the location of the needle tip eliminates the need for use of traditional needle guides and techniques such as the use of a guide wire. Use of a guide wire can lead to complications such as tissue lesions and loss of the tracheostomy pathway because of inadvertent kinking and displacement of the guide wire.

Proper location of needle 12 is achieved when dilation device 18 extends across the pretracheal tissue and tracheal wall. Once needle 12 has entered the tracheal lumen and is properly positioned, dilation device 18 is able to atraumatically dilate the initial needle formed tracheostoma to such a degree that the stoma may receive a tracheostomy canula 22. Dilation device 18 is preferably secured to and about needle 12 and is positioned on the needle such that dilation device 18 extends across the tracheal wall and pretracheal tissues when the tip of the need reaches its most forward position for the procedure. Such placement permits the dilation of the tracheostoma along its entire length from the skin surface to through the tracheal wall.

Figure 3:
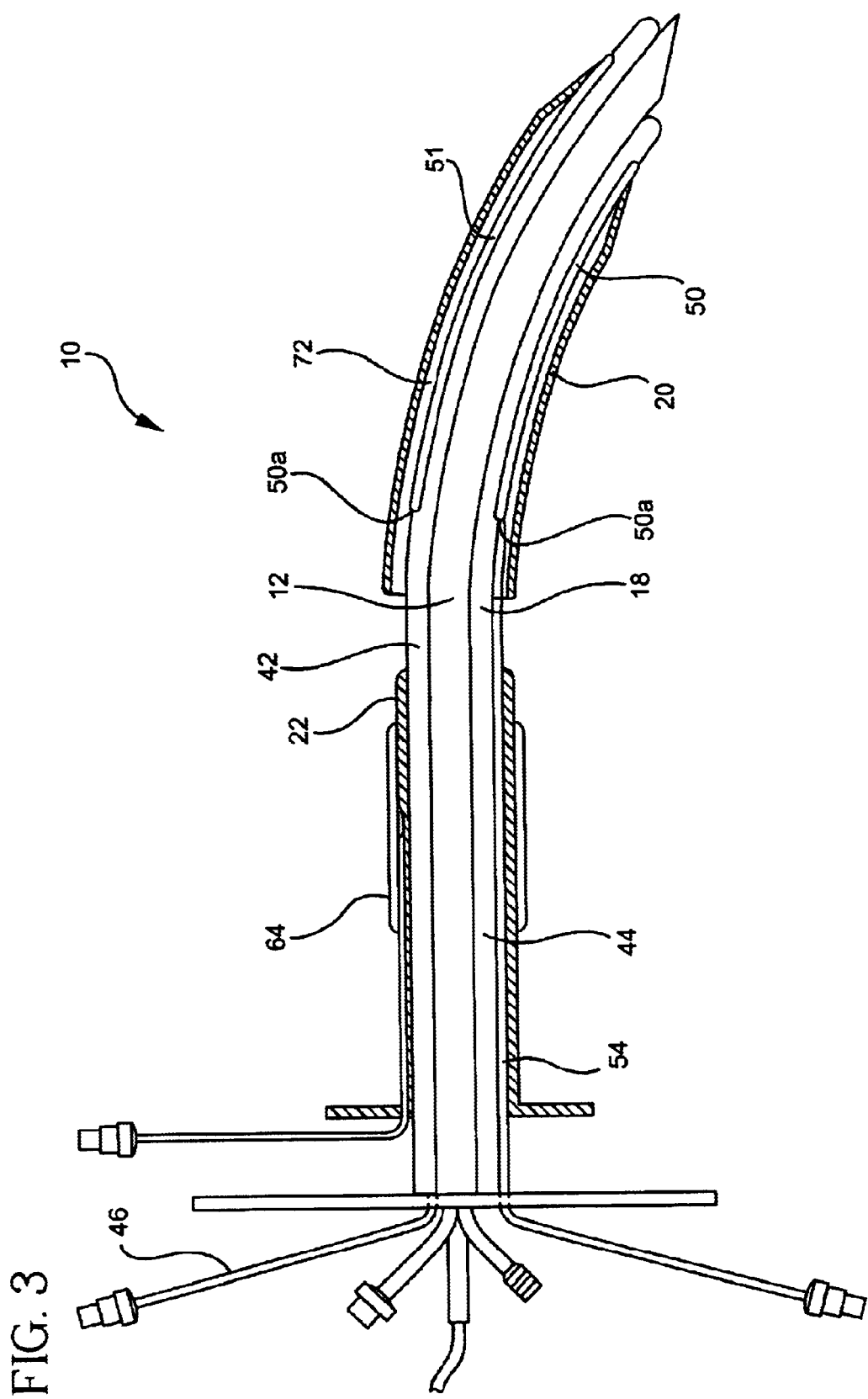
FIG. 3 is a side longitudinal cross-sectional view of the ostomy device of FIG. 1 showing the primary dilator in the dilated position.
Figure 4:
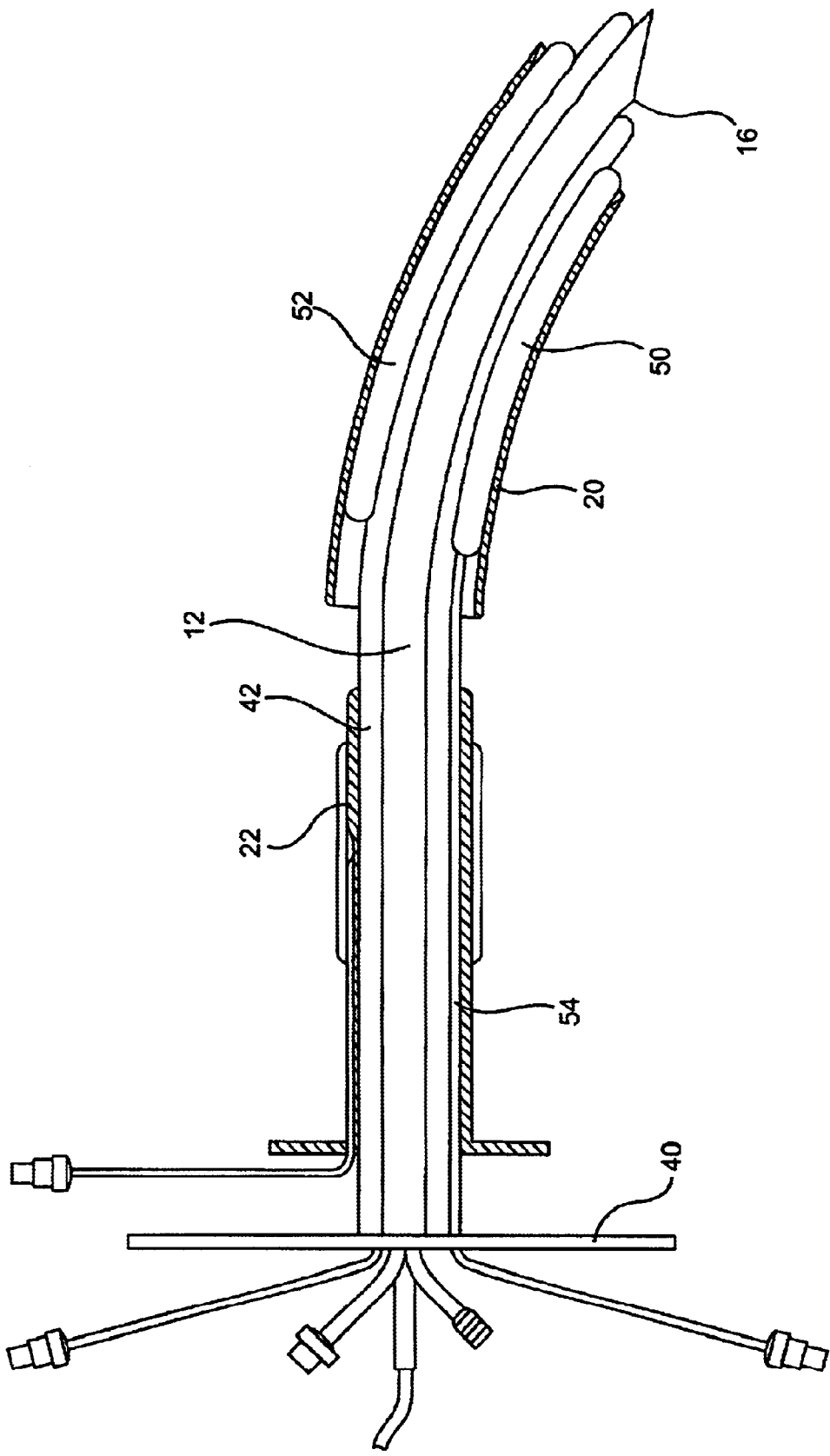
FIG. 4 is a side longitudinal cross-sectional view of the ostomy device of FIG. 1 showing the primary and secondary dilators in the dilated position.
Figure 5:
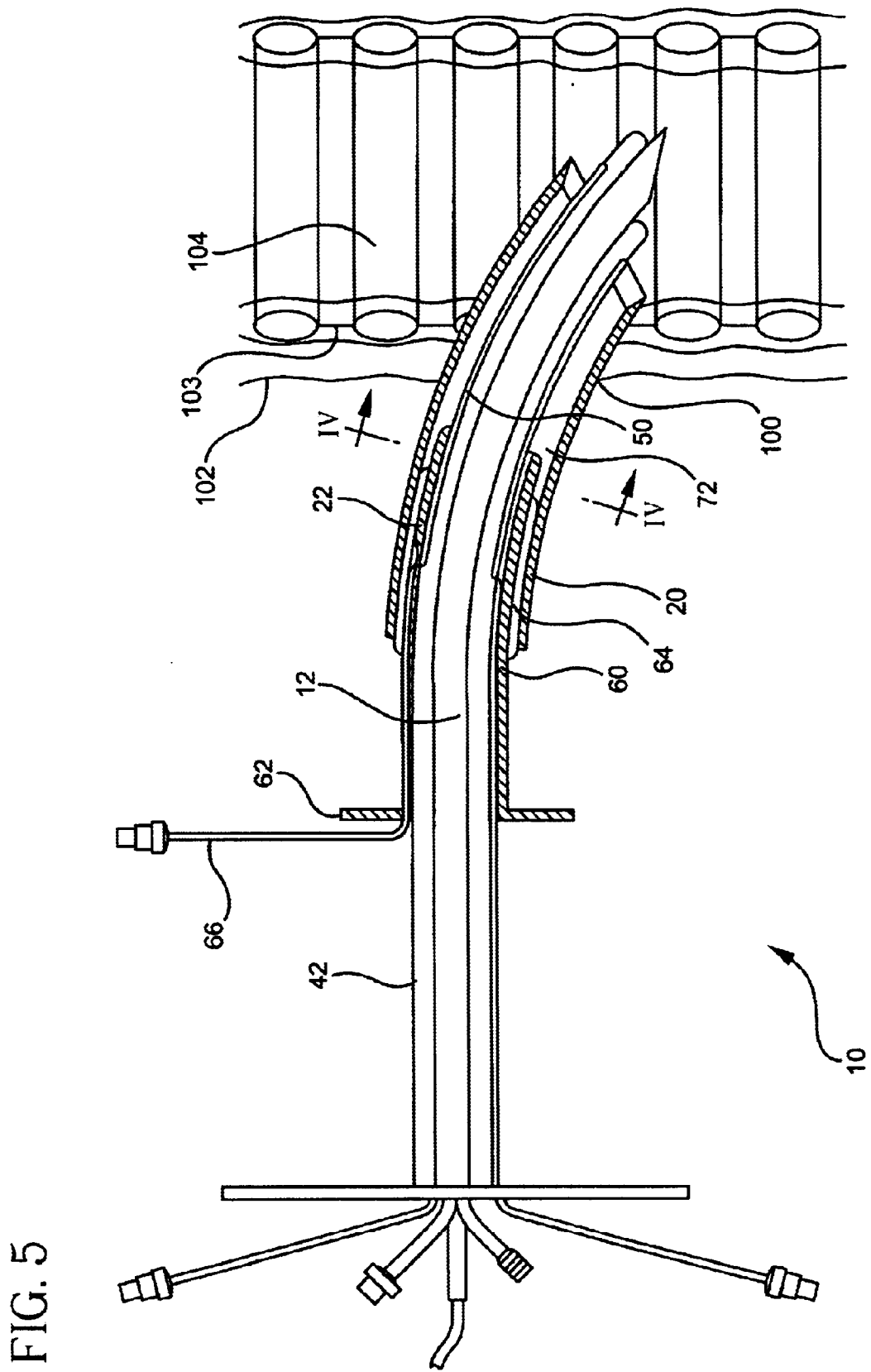
FIG. 5 is a side cross-sectional view of the ostomy device of FIG. 1 showing the canula advanced along the needle toward the tracheal lumen.

With reference to FIGS. 3, 4 and 5, in the preferred embodiment, dilation device 18 may include a primary dilator 42 in the form of an annular sleeve-like chamber 44 extending over a substantial portion of the length of needle 12. Chamber 44 is inflatable causing primary dilator 42 to diametrically radially expand in the radial direction out from needle 12. In order to permit such radial expansion, primary dilator 42 is preferably formed of a malleable material expandable upon the introduction of a fluid such as air or liquid into chamber 44. Fluid may be introduced into chamber 44 through a flexible tube 46 attached to the proximal end of primary dilator 42 and a first pressure source (not shown). Primary dilator 42 provides a first degree of diametrical expansion of the stoma.

Dilation device 18 further includes a secondary dilator 50 concentrically disposed about primary dilator 42 and attached thereto. Secondary dilator 50 may be inflated to enlarge the needle created stoma 100 extending from the skin surface 102 through the tracheal wall 103 and into the tracheal lumen 104. Secondary dilator 50 extends over needle distal portion 14 ending just short of needle tip 16. Secondary dilator 50 preferably has a longitudinal dimension of 5–6 cm, which is sufficient to dilate the tissue passage between the skin surface and tracheal wall in most individuals. Secondary dilator 50 preferably includes an inflatable bladder 52 having radially expandable surface 51 to dilate the stoma. The secondary dilator is preferably formed of a malleable material having a diameter that radially expands upon the introduction of fluid into the bladder.

Secondary dilator 50 may be secured to primary dilator 42 such that the distal and proximal edge 50a taper toward the outer surface of primary dilator 42. This assists in protecting secondary dilator 50 from canula 22 which is slide over primary dilator during the implanting of canula 22 in the trachea. Secondary dilator may be in fluid communication to a second fluid source through a conduit 54 extending from the proximal end of needle 12. The first and second fluid sources for both the primary and secondary dilators 42 and 50 may be a syringe, pump, or other pressure-generating devices. Secondary dilator 50 provides a second degree of diametrical expansion that is preferably greater than that provided by primary dilator 42. Both the primary and secondary dilators 42 and 50 may be slowly and evenly inflated to reduce trauma to the tissues surrounding dilation device 18.

In addition, primary and secondary dilators 42 and 50 are preferably formed such that their combined maximum diametrical expansion is the proper amount for the degree of dilation required. Maximum dilation is preferably just larger than the outside diameter of the canula 22. Therefore, when the dilators stop expanding, proper dilation has been achieved. Accordingly, the operator can easily visually determine when the correct amount of dilation is reached. To achieve this, the primary and secondary dilators may be formed of a flexible but inelastic material.

Figure 6:
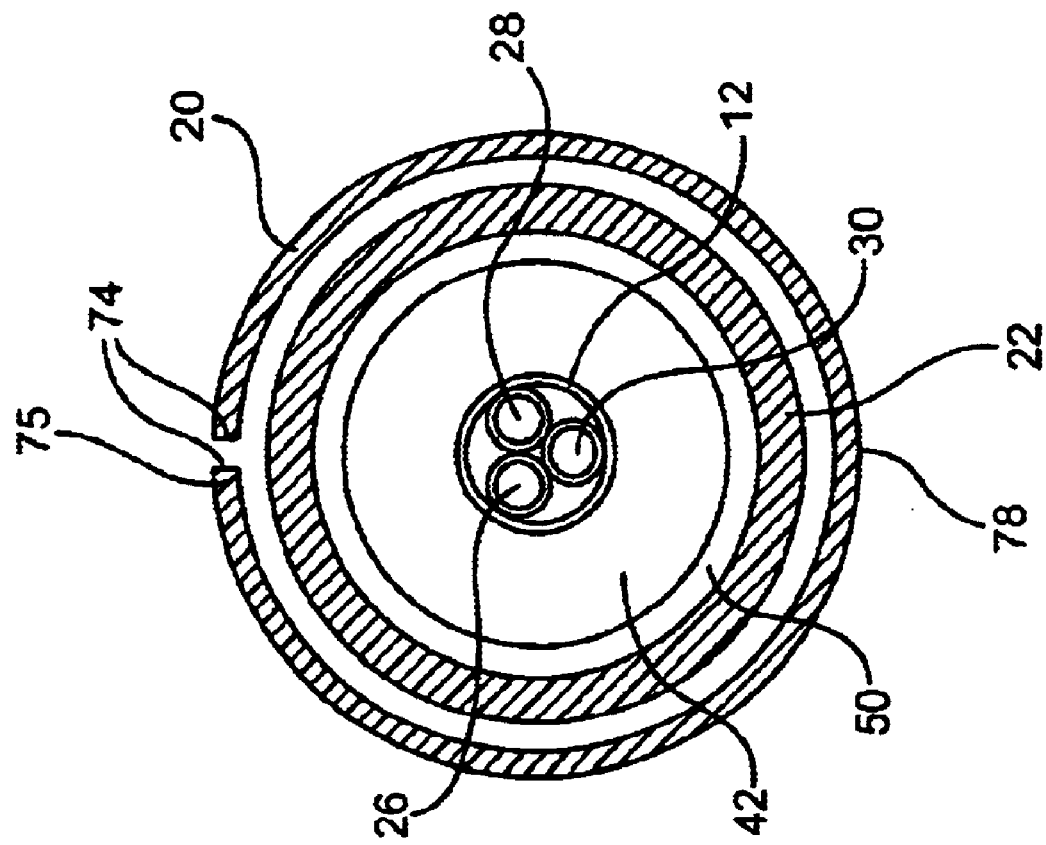
FIG. 6 is a cross-sectional view taken along line VI—VI of FIG. 5.
Figure 7:
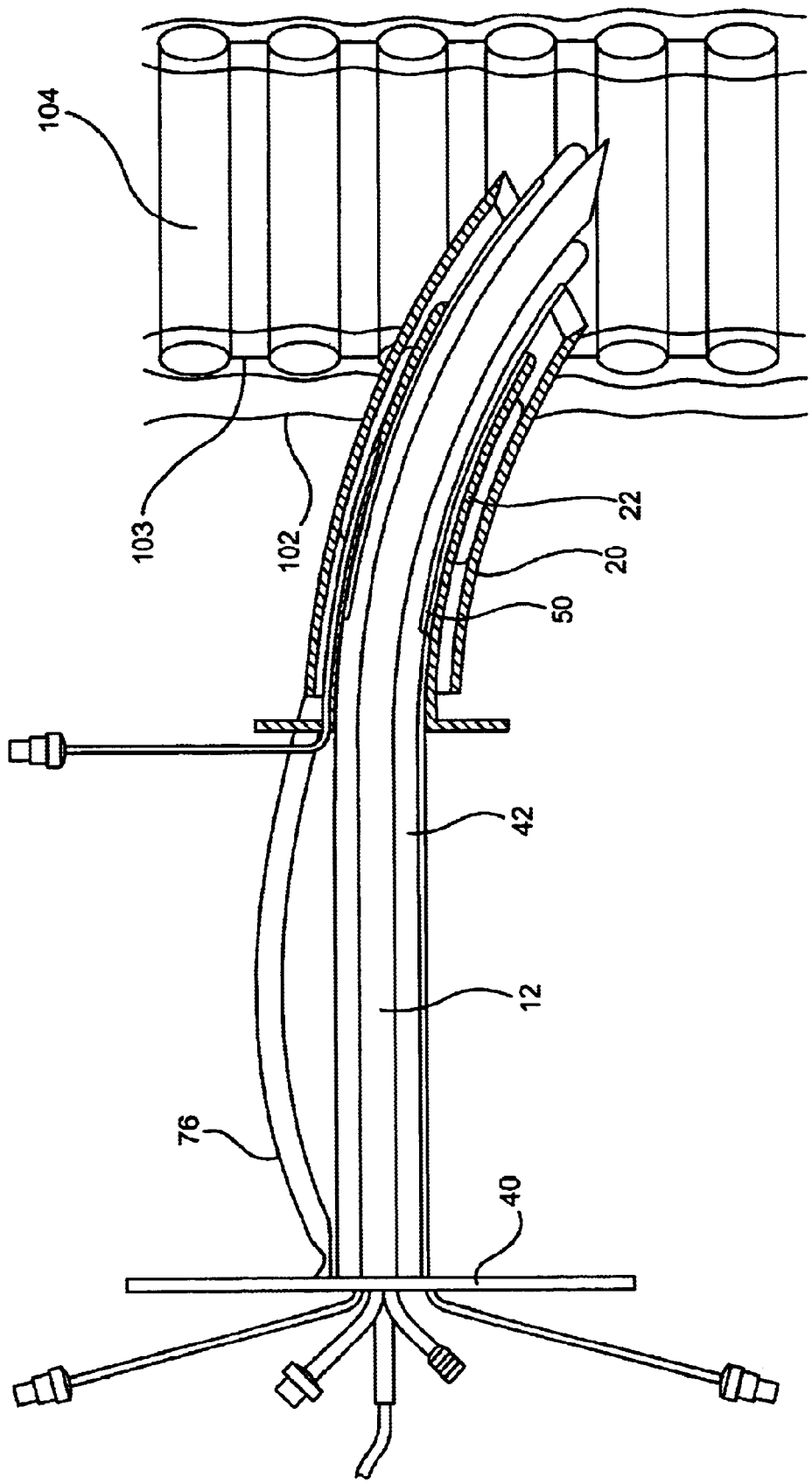
FIG. 7 is a side longitudinal cross-sectional view of the ostomy device of the present invention showing the canula advanced along the needle toward and into the tracheal lumen.

Referring to FIGS. 5, 6 and 7, after the stoma 100 has been dilated, ostomy device 10 may then be employed to implant canula 22 into the tracheal lumen 104. Tracheostomy canula 22 is loaded on needle 12 prior to the start of the procedure by sliding the needle and dilation device 18 through the center of canula 22. At the start of the procedure, canula 22 is positioned along the straight proximal portion of needle 12. Canula 22 may be of a typical commercially available design having a somewhat flexible tubular body 60 extending from a radially extending stop flange 62. A distal end portion of tube 60 may include an inflatable retainer cuff 64 having a fill tube 66 attached thereto to permit fluid to enter cuff 64. Cuff 64 may be inflated after the canula is fully implanted in order to retain canula 22 within the trachea as is well known in the art. As with standard tracheostomy canulas, canula 22 may have a curved shape to extend downwardly in the tracheal lumen once it is implanted. The flexible nature of the tube 60 permits canula 22 to conform to both the straight and curved portions of needle 12. In addition, canula tube 60 preferably has an inside diameter that is slightly greater than the maximum diameter of the inflated primary dilator 42 such that canula 22 may slide in a guided manner over primary dilator 42. Once implanted, canula 22 provides an unrestricted passageway into the tracheal lumen. In manner well known in the art, the implanted canula 22 may be attached to a ventilation device to provide oxygen to the patient in a controlled manner.

Figure 8:
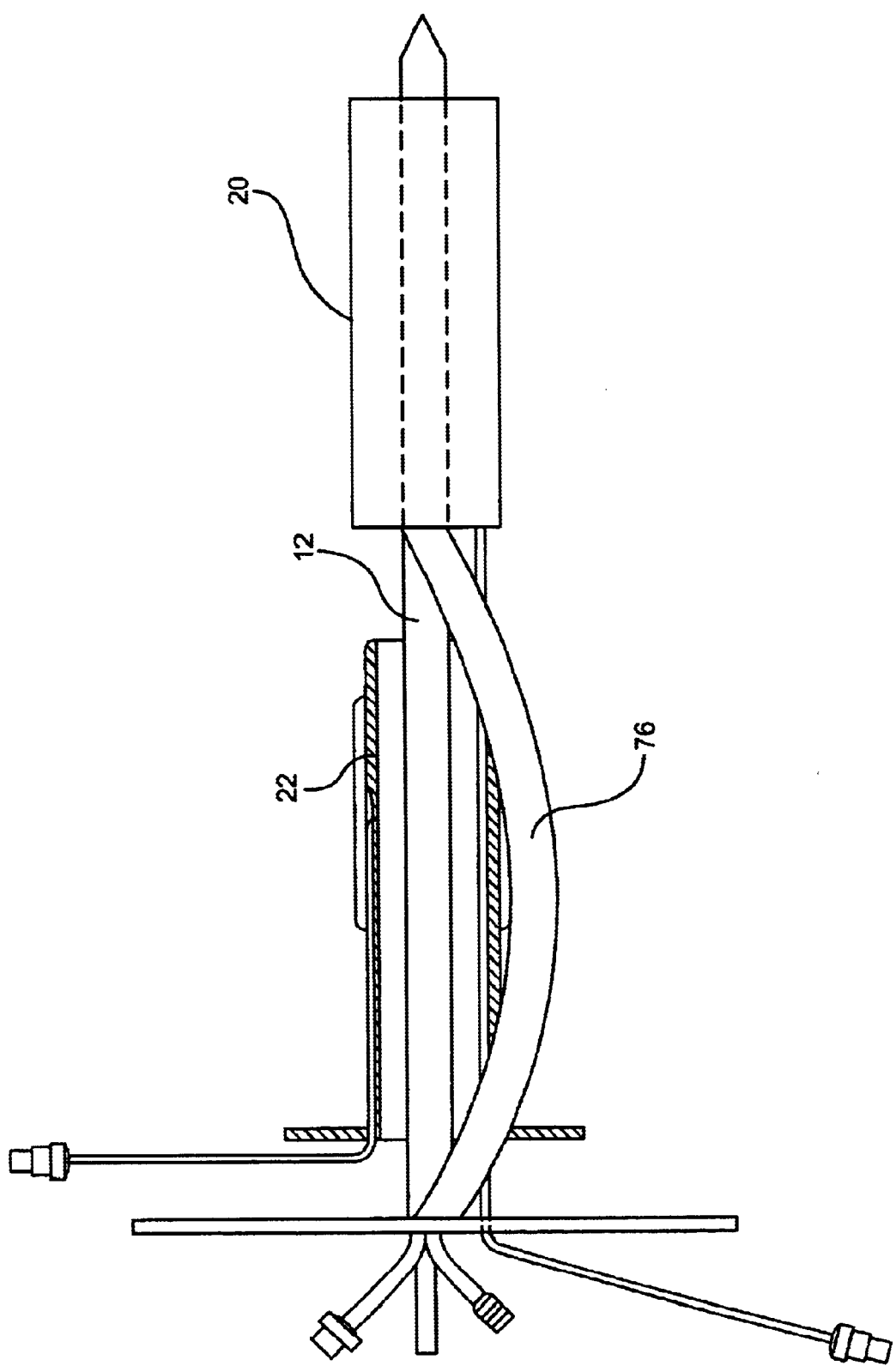
FIG. 8 is a top longitudinal cross-sectional view of the ostomy device of the present invention.

In order to guide canula 22 through the pretracheal tissues and tracheal wall and to protect the surrounding tissues during the implantation, a protective sheath 20 may be provided. Sheath 20 may be positioned over needle 12 adjacent secondary dilator 50 and be expandable radially such that it may expand under the influence of dilation device 18. Sheath 20 may extend proximally from just behind needle tip 16 to a point behind secondary dilator proximal edge 50b. Accordingly, the entire percutaneous passage is lined by sheath 20. A space 72 may be formed between sheath 20 and dilation device 18 when deflated to provide a passage to guide canula 22 as it is advanced into the dilated stoma. Sheath 20 may be removably attached to handle 40 by a flangible member 76 as shown in FIGS. 7 and 8.

Once canula 22 is in place, sheath 20 may be removed from the site. In order to permit radial expansion and removal, sheath may be formed of a smooth material which is essentially rolled along its length forming an open ended hollow tube-like structure. The longitudinal edges 74 of the structure overlap to such a degree that even when the sheath is at its maximum expanded state, a substantially uninterrupted wall is present between secondary dilator 50 and the tracheal wall. When expanded, a slit 75 is present between the edges 74 of the sheath 20. Slit 75 may be enlarged by traction on the opposite end 78 of sheath 20, in such a manner as to accommodate the width of the tracheal canula 22. This will allow removing sheath 20 from around canula 22 and dilatation device 18, by unwrapping and sliding sheath 20. Removal may be facilitated by using flangible member 76 (FIG. 7) that is attached to end 78 of sheath 20.

The operation of the ostomy device 10 of the present invention will now be described. Prior to the beginning of the procedure, channels 26, 28 and 30 may be connected to the syringe, $CO_2$ monitor and fibroscope as desired. Needle tip 16 may used to puncture the skin after which needle 12 may be advanced toward the tracheal lumen. The syringe may aspirate fluid in front of tip 16 as the needle is advanced. As the needle tip passes through the tracheal wall, the resultant $CO_2$ level rise will be detected by the $CO_2$ monitor, indicating to the operator that the needle has entered the tracheal lumen. Images from the fibroscope may be used to confirm intratracheal position and assist the operator in advancing the needle to its forward most position. After the proper intratracheal positioning of the needle is confirmed, the dilation process may begin.

In the preferred embodiment, dilation of the stoma is a two-step controlled progressive dilatation with needle 12 remaining in place. First, the chamber of primary dilator 42 is inflated with fluid creating a radial expansion a small degree less than the size of the inner diameter of tracheostomy canula 22. Such expansion provides some dilation of the stoma and also provides a guide over which canula may travel. In a second step, further dilatation is achieved by inflating secondary dilator 50. The radial expansion of secondary dilator 50 further dilates the stoma to its maximum degree of dilation which is slightly larger than the outer diameter of the tracheostomy canula 22 which will be implanted, allowing atraumatic insertion of the tracheostomy canula.

During the dilatation process, the inflating secondary dilator 50 deforms and enlarges sheath 20. After sufficient dilatation is achieved, secondary dilator 50 is deflated and the tracheostomy canula 22 may be slidingly advanced over the primary and secondary dilator 42 and 50 into the space 72 between secondary dilator 50 and sheath 20. The primary dilator 42 serves as a canula guide while outer sheath 20 protects the delicate pretracheal tissues and tracheal wall, preventing false passages or the rupture of tracheostomy canula cuff 64. Once canula is in place, cuff 46 may be inflated to assist in retaining canula 22 in the proper position. By predilating the stoma, canula 22 may be inserted through the tracheal wall without inflicting undue trauma to the site.

After the tracheostomy canula 22 is implanted, primary dilator 42 may be deflated and needle 12 along with dilation device 18 may be withdrawn from canula 22. Next sheath 20 may be removed by unwrapping as previous described. Due to sheath's rolled construction, it may essentially be unwrapped from around canula stop flange 62 as it is withdrawn from the tracheal wall. The ability of sheath 20 to diametrically expand and be removable over canula flange 62 could also be achieved by a tube (not shown) having a longitudinal split with overlapping edges. Once sheath 20 is removed, canula 22 is secured by the progressive narrowing of the pretracheal tissues along the passage created between the skin and trachea.

Figure 9:
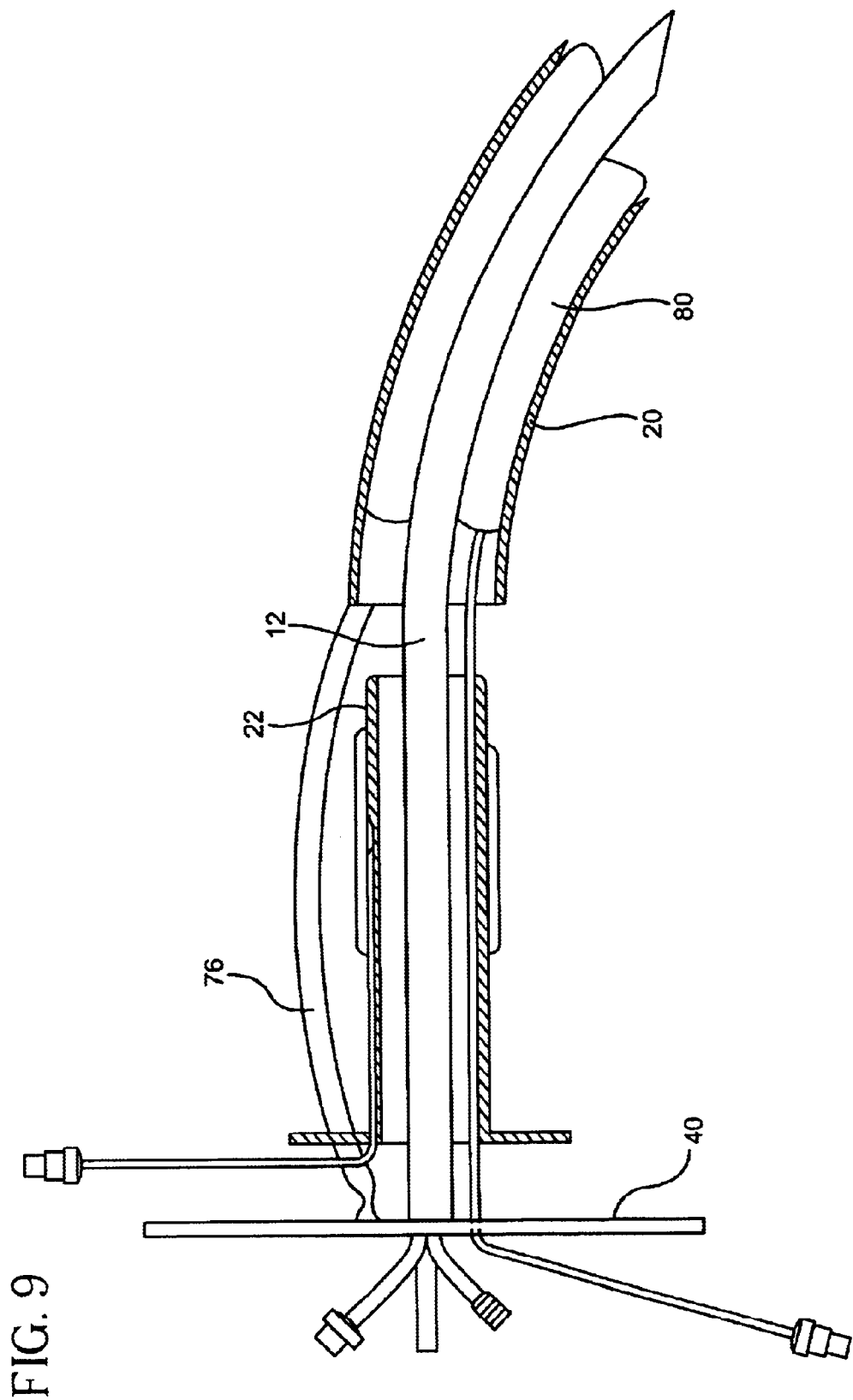
FIG. 9 is a side longitudinal cross-sectional view of an alternative embodiment of the ostomy device of the present invention.

The present invention further contemplates the use of a dilation device having only one inflatable dilator. In this alternative embodiment, shown in FIG. 9, dilator 80 has a shape and construction similar to that of secondary dilator 50 described above. Dilator 80, however, is attached directly to needle 12 and has a somewhat greater diametrical expansion in order to dilate the needle formed stoma. The procedure would also be similar to that set forth above with the absence of the two separate dilation stages. In the alternative embodiment, dilator 80 is inflated gradually to achieve the proper degree of dilation for insertion of canula 22.

Accordingly, the present invention permits proper positioning of needle 12 and dilation device 18, 80 within the tracheal lumen without the need for a guide wire or the use of a bronchoscope. No other device or instrument need be placed within the patient during the procedure thereby reducing the risk of complications. The present invention also permits the stoma to be atraumatically dilated such that a canula may be inserted to provide an unobstructed passage.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An ostomy device comprising:
    an elongate needle having a sharpened tip for percutaneous entry of a body forming a stoma;
    said needle including a plurality of channels extending axially through said needle, each of said plurality of channels having a distal open end adjacent said needle tip; and
    a dilation device disposed about said needle and insertable within the stoma, said dilation device including a radially expandable surface to dilate the stoma for atraumatic receipt of a canula.

2. An ostomy device as defined in claim 1, wherein one of said plurality of channels is adapted to be connected to a syringe, such that fluid in front of the needle tip can be aspirated.

3. An ostomy device as defined in claim 1, wherein one of said plurality of channels is includes a connector which is adapted to be connected to a $CO_2$ monitor.

4. An ostomy device as defined in claim 1, wherein said one of said plurality of channels is adapted to receive a fibroscope.

5. An ostomy device as defined in claim 1, wherein said dilation device includes a first dilator including an inflatable member, said first dilator being in fluid communication with a first fluid source, such that introduction of fluid in said first dilator results in radial expansion thereof.

6. An ostomy device as defined in claim 5, wherein said dilation device includes a second dilator radially disposed about a portion of said first dilator.

7. An ostomy device as defined in claim 6, wherein said first dilator is radially expandable to create a first degree of dilation and said second dilator is expandable to create a second degree of dilation greater than said first degree of dilation.

8. An ostomy device as defined in claim 6, further including a canula having a tube positioned on said needle and advancable toward said tip when said second dilator is uninflated, and wherein said first and second dilators having a combined diameter equal or greater than a diameter of said canula tube.

9. An ostomy device as defined in claim 8, further including a radially expandable sheath radially disposed about said second dilator, said sheath being expandable upon inflation of said dilation device, said sheath providing a guide for said canula upon advancement in the stoma.

10. An ostomy device as defined in claim 10, wherein said sheath has overlapping longitudinal edges.

11. An ostomy device as defined in claim 1, wherein said first dilator includes an inflatable sleeve having an outer wall and said second dilator being formed about said outer wall, said sleeve being in fluid communication with a first fluid source.

12. A tracheostomy device comprising:
    a needle having an opening extending axially there through and having a sharpened tip for forming a tracheostoma in a tracheal wall;
    an inflatable dilation device being in fluid communication with a fluid source and being secured about said needle and insertable within the tracheostoma, said dilation device including a surface being radially expandable upon introduction of a fluid to dilate the tracheostoma for receiving a tracheostomy canula; and
    a radially expandable sheath disposed about said dilation device, said sheath being radially expandable upon expansion of said dilation device.

13. A tracheostomy device as defined in claim 12, further including a tracheostomy canula disposed about said needle and advancable along said needle toward said tip between said dilation device and said sheath, said sheath protecting pretrachael and tracheal tissues defining the tracheostoma upon insertion of said canula into the trachea.

14. A tracheostomy device as defined in claim 13, wherein said sheath includes a member having overlapping edges to provide a continuous wall upon diametrical expansion by said dilation device.

15. A tracheostomy device as defined in claim 12, wherein said sheath includes a longitudinal slit extending along a length thereof to permit diametrical expansion of said sheath.

16. A tracheostomy device as defined in claim 12, wherein said needle opening includes a plurality of channels extending axially there through.

17. A tracheostomy device as defined in claim 16, wherein said plurality of channels each include a distal end positioned adjacent said needle tip and a proximal end said proximal end of one of said plurality of channels being operatively connected to a syringe.

18. A tracheostomy device comprising:
a needle having a passage extending axially there through and having a distal portion ending in a sharpened tip for forming a stoma in a tracheal wall;
a dilation device adapted to be inserted in the tracheostoma and including a first dilator disposed about said needle and being diametrically expandable to provide a first degree of stoma dilation;
the dilation device further including a second dilator disposed radially about said first dilator and adjacent said distal end of said needle and being insertable within the stoma, said second dilator including a diametrically expandable surface to provide a second degree of stoma dilation whereby the stoma is capable of a traumatically receiving a tracheostomy canula.

19. A tracheostomy device as defined in claim 18, wherein said first dilator includes an inflatable sleeve that radially expands upon introduction of a fluid.

20. A tracheostomy device as defined in claim 19, wherein said second dilator includes an inflatable chamber that radially expands upon introduction of a fluid.

21. A tracheostomy device as defined in claim 19, wherein said second dilator extends over the distal portion of said needle.

22. A tracheostomy device as defined in claim 18, further including a tracheostomy canula disposed about said needle and advancable along said needle over said dilation device toward said tip for insertion in the dilated stoma.

23. A tracheostomy device as defined in claim 18, a radially expandable sheath disposed about said dilation device, said sheath being diametrically expandable upon expansion said dilatation device.

24. A tracheostomy device as defined in claim 18, wherein said needle passage includes a plurality of channels extending axially there through.

25. An ostomy device comprising:
an elongate needle having a sharpened tip for percutaneous entry of a body forming a stoma;
said needle including a plurality of channels extending axially through said needle, each of said plurality of channels having a distal end adjacent said needle tip;
a dilation device disposed about said needle and insertable within the stoma, said dilation device including a radially expandable surface to dilate the stoma for atraumatic receipt of a canula; and
a radially expandable sheath radially disposed about said dilation device, said sheath having overlapping longitudinal edges, said sheath being expandable upon inflation of said dilation device, said sheath providing a guide for the canula upon advancement in the stoma.

26. A tracheostomy device comprising:
a needle having an opening extending axially there through and having a sharpened tip for forming a tracheostoma in a tracheal wall;
an inflatable dilation device being in fluid communication with a fluid source and being secured about said needle and insertable within the tracheostoma, said dilation device including a surface being radially expandable upon introduction of a fluid to dilate the tracheostoma for receiving a tracheostomy canula;
a radially expandable sheath disposed about said dilation device, said sheath being radially expandable upon expansion of said dilation device, said sheath including a member having overlapping edges to provide a continuous wall upon diametrical expansion by said dilation device; and
a tracheostomy canula disposed about said needle and advancable along said needle toward said tip between said dilation device and said sheath, said sheath protecting pretrachael and tracheal tissues defining the tracheostoma upon insertion of said canula into the trachea.

27. A tracheostomy device comprising:
a needle having an opening extending axially there through and having a sharpened tip for forming a tracheostoma in a tracheal wall;
an inflatable dilation device being in fluid communication with a fluid source and being secured about said needle and insertable within the tracheostoma, said dilation device including a surface being radially expandable upon introduction of a fluid to dilate the tracheostoma for receiving a tracheostomy canula; and
a radially expandable sheath disposed about said dilation device, said sheath including a longitudinal slit extending along a length thereof to permit diametrical expansion of said sheath, said sheath being radially expandable upon expansion of said dilation device.

28. A tracheostomy device comprising:
a needle having an opening extending axially there through and having a sharpened tip for forming a tracheostoma in a tracheal wall;
an inflatable dilation device being in fluid communication with a fluid source and being secured about said needle and insertable within the tracheostoma, said dilation device including a surface being radially expandable upon introduction of a fluid to dilate the tracheostoma for receiving a tracheostomy canula; and
a radially expandable sheath disposed about said dilation device and removably connected to said needle by a frangible member, said sheath being radially expandable upon expansion of said dilation device.

29. A method of implanting a tracheal canula comprising the steps of:
providing a tracheostomy device including a needle having a plurality of channels extending longitudinally there through and operatively connecting one of said plurality of channels to a monitoring device, said needle having a sharpened tip and having a diametrically expandable dilator disposed about the needle;
positioning a tracheal canula over the tracheostomy device;

inserting the needle through the tracheal wall without the use of a guide wire to form a tracheostoma;

monitoring the conditions at the needle tip during insertion of the needle in order to determine the anatomical location of the needle tip;

expanding the dilator to atraumatically dilate the tracheostoma;

contracting the dilator;

advancing the canula over the needle into the dilated tracheostoma; and removing the tracheostomy device from the tracheostoma.

30. A method of dilating a stoma comprising the steps of:

providing a ostomy device including a needle having a sharpened tip and having a diametrically expandable dilation device disposed about the needle, the dilation device including a first and second inflatable dilator;

inserting the needle through a body wall to form a stoma;

advancing the needle until said dilation device is received within the stoma;

inflating the first dilator to dilate the stoma a first degree; and inflating the second dilator to further dilate the stoma a second degree.

31. The method of as defined in claim 30 further comprising the steps of providing said second dilator disposed radially about said first dilator.

* * * * *